United States Patent
Hawkes et al.

(10) Patent No.: US 12,280,208 B2
(45) Date of Patent: Apr. 22, 2025

(54) VINE ROBOT TRACHEAL INTUBATION DEVICE

(71) Applicants: The Regents of the University of California, Oakland, CA (US); The Board of Trustees of the Leland Stanford Junior University, Stanford, CA (US)

(72) Inventors: Elliot W. Hawkes, Goleta, CA (US); David A. Haggerty, Goleta, CA (US); David R. Drover, Stanford, CA (US)

(73) Assignees: The Regents of the University of California, Oakland, CA (US); The Board of Trustees of the Leland Stanford Junior University, Stanford, CA (US)

( * ) Notice: Subject to any disclaimer, the term of this patent is extended or adjusted under 35 U.S.C. 154(b) by 548 days.

(21) Appl. No.: 17/632,335

(22) PCT Filed: Jul. 29, 2020

(86) PCT No.: PCT/US2020/043942
§ 371 (c)(1),
(2) Date: Feb. 2, 2022

(87) PCT Pub. No.: WO2021/025911
PCT Pub. Date: Feb. 11, 2021

(65) Prior Publication Data
US 2022/0288334 A1  Sep. 15, 2022

Related U.S. Application Data
(60) Provisional application No. 62/882,239, filed on Aug. 2, 2019.

(51) Int. Cl.
  *A61M 16/04*  (2006.01)
  *A61M 16/10*  (2006.01)
  *A61M 25/01*  (2006.01)

(52) U.S. Cl.
  CPC ....... *A61M 16/049* (2014.02); *A61M 16/1005* (2014.02); *A61M 25/0119* (2013.01); *A61M 2205/0266* (2013.01)

(58) Field of Classification Search
  CPC ............ A61M 16/0488; A61M 16/049; A61M 16/0493; A61M 25/0119;
  (Continued)

(56) References Cited

U.S. PATENT DOCUMENTS

| | | | |
|---|---|---|---|
| 3,506,011 A | 4/1970 | Silverman | |
| 4,077,610 A | 3/1978 | Masuda | |
| (Continued) | | | |

OTHER PUBLICATIONS

Hawkes et al, "A soft robot that navigates its environment through growth", Science Robotics, eaan, vol. 2, No. 8, pp. 1-7, Jul. 19, 2017 (Year: 2017).*

(Continued)

*Primary Examiner* — Colin W Stuart
*Assistant Examiner* — Douglas Y Sul
(74) *Attorney, Agent, or Firm* — Greer, Burns & Crain, Ltd.; Steven P. Fallon

(57) ABSTRACT

An everting vine robot intubation device capable of automatically and autonomously intubating the trachea and producing a lumen through which artificial ventilation may be conducted. The device includes an everting primary vine
(Continued)

robot attached to a mouthpiece and a smaller diameter everting intubation vine robot associated with the primary everting vine robot. The primary vine robot is shaped and sized to extend to the back of a patient's laryngopharynx when fully actuated and the intubation everting vine robot is shaped and sized to extend from the primary vine robot into the patient's trachea when fully actuated.

21 Claims, 8 Drawing Sheets

(58) Field of Classification Search
CPC ... A61M 2025/1065; A61M 2205/0266; F16L 55/165; F16L 55/1651; F16L 55/18
USPC .......................................................... 138/98
See application file for complete search history.

(56) References Cited

U.S. PATENT DOCUMENTS

| | | | | |
|---|---|---|---|---|
| 4,231,365 | A | * | 11/1980 | Scarberry ......... A61M 16/0415 128/207.15 |
| 5,339,805 | A | * | 8/1994 | Parker ............... A61M 16/0409 128/207.14 |
| 6,978,784 | B2 | | 12/2005 | Pekar |
| 2001/0044595 | A1 | * | 11/2001 | Reydel ............. A61M 25/0668 604/523 |
| 2002/0016607 | A1 | * | 2/2002 | Bonadio ............ A61M 25/0119 606/192 |
| 2005/0268917 | A1 | * | 12/2005 | Boedeker .............. A61M 16/04 128/207.14 |
| 2007/0203472 | A1 | * | 8/2007 | Nachmani ......... A61M 25/0662 604/523 |
| 2015/0151063 | A1 | * | 6/2015 | Hoftman .................. A61B 1/05 128/200.26 |
| 2016/0227991 | A1 | | 8/2016 | Hayut et al. |
| 2016/0262603 | A1 | * | 9/2016 | Molnar .................. A61B 1/233 |
| 2017/0216545 | A1 | * | 8/2017 | Avitsian ............ A61M 16/0488 |
| 2018/0104427 | A1 | * | 4/2018 | Avitsian ............ A61M 16/0486 |
| 2019/0217908 | A1 | | 7/2019 | Hawkes et al. |
| 2021/0354289 | A1 | | 11/2021 | Hawkes et al. |

OTHER PUBLICATIONS

Greer et al. "Series Pneumatic Artificial Muscles (sPAMS) and Application to a Soft Continuum Robot", IEEE Int Conf Autom. 2017: 5503-5510. (Year: 2017).*

Greer et al. "A Soft, Steerable Continuum Robot That Grows via Tip Extension", Soft Robotics, vol. 6, 1:95-108, 2019. (Year: 2019).*

International Search Report and Written Opinion from the corresponding International Patent Application No. PCT/US2020/043942, dated Oct. 8, 2020.

Maladen et al., "Granular lift forces predict vertical motion of a sand-swimming robot", 2011 IEEE International Conference on Robotics and Automation, 2011, pp. 1398-1403, IEEE.

Winter et al., "Teaching RoboClam to Dig: The Design, Testing, and Genetic Algorithm Optimization of a Biomimetic Robot", The 2010 IEEE/RSJ International Conference on Intelligent Robots and Systems, 2010, pp. 4231-4235, IEEE.

Sadeghi et al., "Toward Self-Growing Soft Robots Inspired by Plant Roots and Based on Additive Manufacturing Technologies", Soft Robotics, 2017, pp. 211-223, vol. 4, No. 3, Mary Ann Liebert, Inc.

Nagaoka et al., "Experimental Study on Autonomous Burrowing Screw Robot for Subsurface Exploration on the Moon", 2008 IEEE/RSJ International Conference on Intelligent Robots and Systems, 2008, pp. 4104-4109, IEEE.

Tsinker, "Performance of jetted anchor piles with widening", Journal of the Geotechnical Engineering Division, 1977, pp. 213-226, vol. 103, No. 3, American Society of Civil Engineers.

Koller-Hodac et al., "Actuated Bivalve Robot: Study of the Burrowing Locomotion in Sediment", 2010 IEEE International Conference on Robotics and Automation, 2010, pp. 1209-1214, IEEE.

Zagal et al., "Deformable Octahedron Burrowing Robot", Artificial Life, 2012, pp. 431-438, vol. 13, Massachusetts Institute of Technology.

Sadeghi et al., "Robotic Mechanism for Soil Penetration Inspired by Plant Root", 2013 IEEE International Conference on Robotics and Automation, 2013, pp. 3457-3462, IEEE.

Naclerio et al., "Soft Robotic Burrowing Device with Tip-Extension and Granular Fluidization", 2018 IEEE/RSJ International Conference on Intelligent Robots and Systems (IROS), 2018, pp. 5918-5923, IEEE.

Japanese Office Action (and translation) from the corresponding Japanese Patent Application No. 2023-215381, dated Jul. 30, 2024.

* cited by examiner

VINE ROBOT TRACHEAL INTUBATION DEVICE

PRIORITY CLAIM AND REFERENCE TO RELATED APPLICATION

The application claims priority under 35 U.S.C. § 119 and all applicable statutes and treaties from prior U.S. provisional application Ser. No. 62/882,239, which was filed Aug. 2, 2019.

STATEMENT OF GOVERNMENT INTEREST

This invention was made with government support under grant no. 1637446 awarded by the National Science Foundation. The government has certain rights in the invention.

FIELD

Fields of the invention included medical devices, particularly intubation devices, and robotics.

BACKGROUND

Hawkes et al. US Patent Publication US2019/0217908, Published Jul. 18, 2019 describes a growth robot. The growth robot has a thin-walled, hollow, pressurized, compliant body that elongates the body by everting from its tip new wall material that is stored inside the body and controls the shape of the body by actively controlling the relative lengths of the wall material along opposing sides of the body. Relative lengths of the wall material along opposing sides of the body can be controlled by shortening the length of the wall material on the side facing the inside of a turn by using contracting artificial muscles mounted along the length of the body. Relative lengths of the wall material along opposing sides of the body can also be controlled by lengthening the wall material on the side facing the outside of a turn, by releasing pinches in the wall material, or by actively softening the material so that the body lengthens due to the internal pressure. Relative lengths of the wall material along opposing sides of the body can also be controlled by actively restraining the length of the wall material on the side facing the inside of a turn while allowing the wall material on the outside of the turn to lengthen.

An advancement of the growth robot technology by Hawkes et al. is provided in a soft robotic device that has an apical extension and includes fluid emission for burrowing and cleaning Such soft robots are able to burrow through sand or dirt, in a manner analogous to a plant root. The robot extends apically through eversion, while emitting fluid from the tip that fluidizes sand and soil making it possible to grow underground. That advance is disclosed in PCT/US2019/50998, filed Sep. 13, 2019 and in the published paper by Hawkes et al., entitled "Soft Robotic Burrowing Device with Tip-Extension and Granular Fluidization.

Emergency Medical Technicians (EMTs) only achieve just over 50% success with tracheal intubation in emergency scenarios, for various reasons. To achieve the high level of success realized in hospital rooms, extensive training is required at prohibitive cost, and as such a serious medical dilemma is observed: how to ensure critical care is effectively provided without an anesthesiologist level training of nurses, paramedics, or EMTs. The present invention can provide for hospital level success with less extensive medical training and is expected to improve success rates for EMTs and other personnel.

SUMMARY OF THE INVENTION

A preferred embodiment provides an everting vine robot intubation device capable of automatically and autonomously intubating the trachea and producing a lumen through which artificial ventilation may be conducted. The device includes an everting primary vine robot attached to a mouthpiece and a smaller diameter everting intubation vine robot associated with the primary everting vine robot. The primary vine robot is shaped and sized to extend to the back of a patient's laryngopharynx when fully actuated and the intubation everting vine robot is shaped and sized to extend from the primary vine robot into the patient's trachea when fully actuated.

A method for intubation of a patient is provided. A mouthpiece attached to an everting primary vine robot and an intubation vine robot with both of the primary vine robot and an intubation vine robot in an unactuated position is inserted into the patient's mouth. Fluid pressure is applied into the primary vine robot to gradually evert and extend it into the back of the laryngopharynx of the patient. Fluid pressure is applied to extend the intubation vine robot into the trachea of the patient and provide a lumen from the mouthpiece to the trachea. Air or oxygen is provided through the lumen into the trachea.

BRIEF DESCRIPTION OF THE DRAWINGS

The invention will be explained in greater detail hereinafter on the basis of exemplary embodiments illustrated in the drawings, in which.

DESCRIPTION OF THE PREFERRED EMBODIMENTS

Figure 1A:
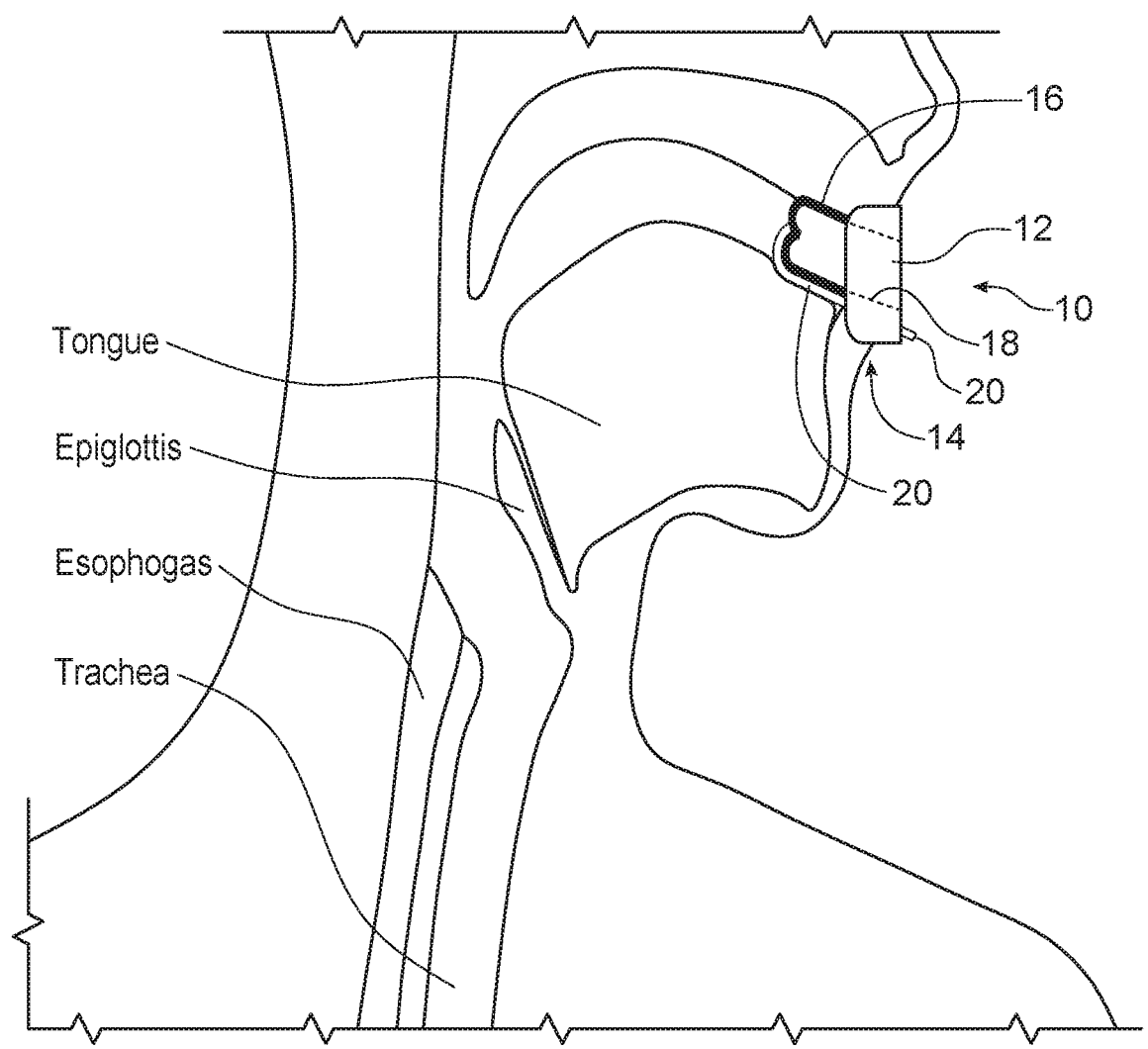
FIG. 1A is a schematic diagram of a preferred embodiment vine robot intubation device in an un-actuated state.

A preferred embodiment vine robot intubation device includes, and preferably consists of, a main eversion body, an intubation body, and a mouthpiece with a an access port to permit fluid/pressure transfer into the bodies from a regulated pressure reservoir. The main eversion body grows down the throat when inflated and carries the intubation body past the tongue and epiglottis. After primary inflation, the intubation body is inflated to grown into the trachea beyond the epiglottis. This body can act as a pathway through which a semi-rigid breathing tube can be passed to commence artificial breathing. The total length can be predetermined to match different physiology, e.g., by patient size, age, or measured physical characteristics. Preferred embodiments are inexpensive and disposable, avoiding problems regarding cleaning and reuse, which lead to hospital acquired infections and other problems.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

A preferred embodiment vine robot intubation device 10 is illustrated in FIGS. 1A-1-E, in progressive states during an intubation procedure. FIG. 1A shows the initial state and unactuated state, in which a shaped mouthpiece 12 is inserted into the mouth 14 of a patient. The mouthpiece holds a primary vine robot 16 and includes an access port 18 to permit fluid/pressure transfer into the primary vine robot 16 to grow the primary vine robot 16 via eversion. An intubation vine robot 20 is carried on the outer surface of the primary vine robot 16 and extends through the mouthpiece 10 to permit access to fluid/pressure for its separate actuation and eversion. Much of the intubation vine robot 20 is folded within the primary vine robot 16 in FIG. 1A, as the primary vine robot 16 is in its fully retracted state when most of its material is inverted upon itself back inward toward its center. Generally, the diameter and length of both of the primary vine robot and intubation vine robot can be predetermined according to physiology type or measured physical characteristics of a patient being intubated, e.g., age, gender, according to physical measurements of throat structure, etc. In practice, a practitioner can have a selection of vine robot intubation devices available and can use an appropriately sized choice based upon physiology. For material of the primary vine robot 16 and the intubation vine robot 20, biocompatible plastics are preferred. Stiffness is lower than the radial stiffness, such that the body will lengthen with pressurization instead of ballooning outward. Couplings to the mouthpiece and for inflation will be compatible with current medical technology, e.g. a Luer lock. The device is preferably sterilized and packaged for single use, and packaging and device can include markings to ensure proper use by practitioners.

The mouthpiece 12 is preferably formed biocompatible plastic or firm rubber compounds and is molded to match the general anatomy of the human face and mouth, with a protrusion for insertion into the mouth to depress the tongue and a recess into which the teeth can fall to hold the device inside the mouth and set a standard "zero" point reference from which extension of the intubation vine robot 20 can be determined. Preferred materials include medical grade silicone, polyurethane, or polyethylene. A mouthpiece is sized according to anatomical characteristics, as discussed above with respect to the vine robots. The mouthpiece 12 can house mechanical components that allow for actuation (e.g. buttons) and an indicator to show whether or not it has been used. Stiffness is achieved through inflation. The mouthpiece in a preferred embodiment can connect to and/or include a pressure reservoir, an actuation mechanism to commence intubation, and mechanical and electrical elements to actuate and control the two vine robots. The housing also includes a passage through which the semi-rigid breathing tube can be passed down to the trachea through the secondary body. The control can include light, ultrasound, magnetic, or other feedback The primary vine robot 16 is a larger, primary vine robot that delivers the smaller intubation vine robot 20 to the back of the laryngopharynx while producing a jaw thrust that further exposes the trachea. The diameter of the primary vine robot 16 robot is set such that while filling the oral cavity and oropharynx, it lifts the lower jaw and protrudes it forward and down. Fluid, e.g., air, is delivered through the port 18 with sufficient pressure to slowly inflate and invert the primary vine robot 16 until it reaches the back of the laryngopharynx. Once that point is reached, the smaller intubation vine robot 20 is actuated via fluid pressure from its proximal end that extends through the mouthpiece. The primary vine robot 16 can be shaped in a predetermined non-linear shape (when extended) and have material in specific positions to introduce specific pressure points to protrude the mandible, lift the epiglottis, and expose the trachea. Methods for shaping and producing firmness of the material in particular sections are disclosed in Hawkes et al. US Patent Publication US2019/0217908.

The intubation vine robot 20 is a lumen-producing vine robot that grows from the tip of the primary vine robot and accesses the trachea beyond the vestibular folds. By lumen-producing, the intubation vine robot provides an open lumen for passage and terminates distally with the opening or a temporarily sealed distal tip that can be breached or penetrated, such that after complete eversion, it provides an open lumen from its proximal opening to a distal opening. The distal tip can be open or include, e.g. a perforated seal. Another option is an elastic distal tip that the breathing tube can breach and pass through. This type of distal tip provides feedback to a practitioner as to when a breathing tube passes out of the distal tip of the intubation vine roboe. The intubation vine robot 20 is preferably designed to work in a Seldinger type fashion to access the trachea in circumstances where the vocal cords are partially closed. Vine robots have been shown to be able to pass through orifices smaller than their body diameter. With appropriate softness size, the intubation vine robot 20 can pass through partially closed cords regardless of the orifice size, and due to the elimination of relative motion between the rigid ventilation tube and the cords, a larger tube may be passed through this lumen. The intubation vine robot 20 may also be designed in such a way as to produce the artificial breathing passage by hardening, or by pulling a semi-rigid tube through itself while growing, for example. By affixing a rigid tube to the open tip of the intubation body, the inflation acts as a pulling force as the intubation body everts. This allows for the automatic delivery of a rigid tube. Another option is a biologically compatible self-hardening material infused into the fabric of the vine robot bodies, which permits hardening the device inside the body to produce its own rigid lumen. While one intubation vine robot 20 is illustrated, the primary vine robot 20 can carry multiple intubation bodies (e.g., a controlled intubation robot and an uncontrolled/passive simple lumen) intended to increase device robustness, as well as the numerous potential configurations of each.

Figure 1B:
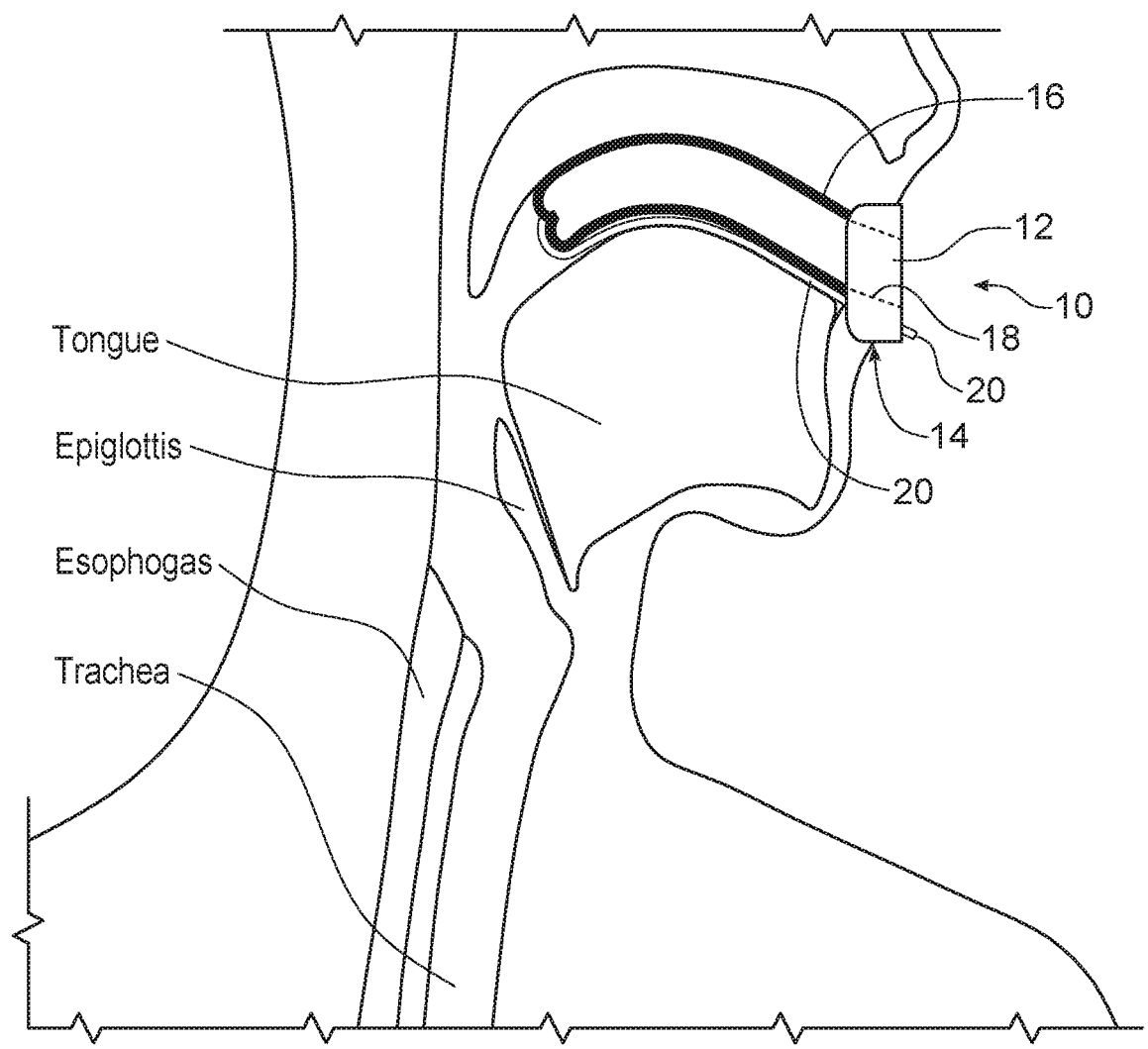
FIGS. 1B and 1C illustrate the vine robot intubation device of FIG. 1A in a partially actuated state.
Figure 1C:
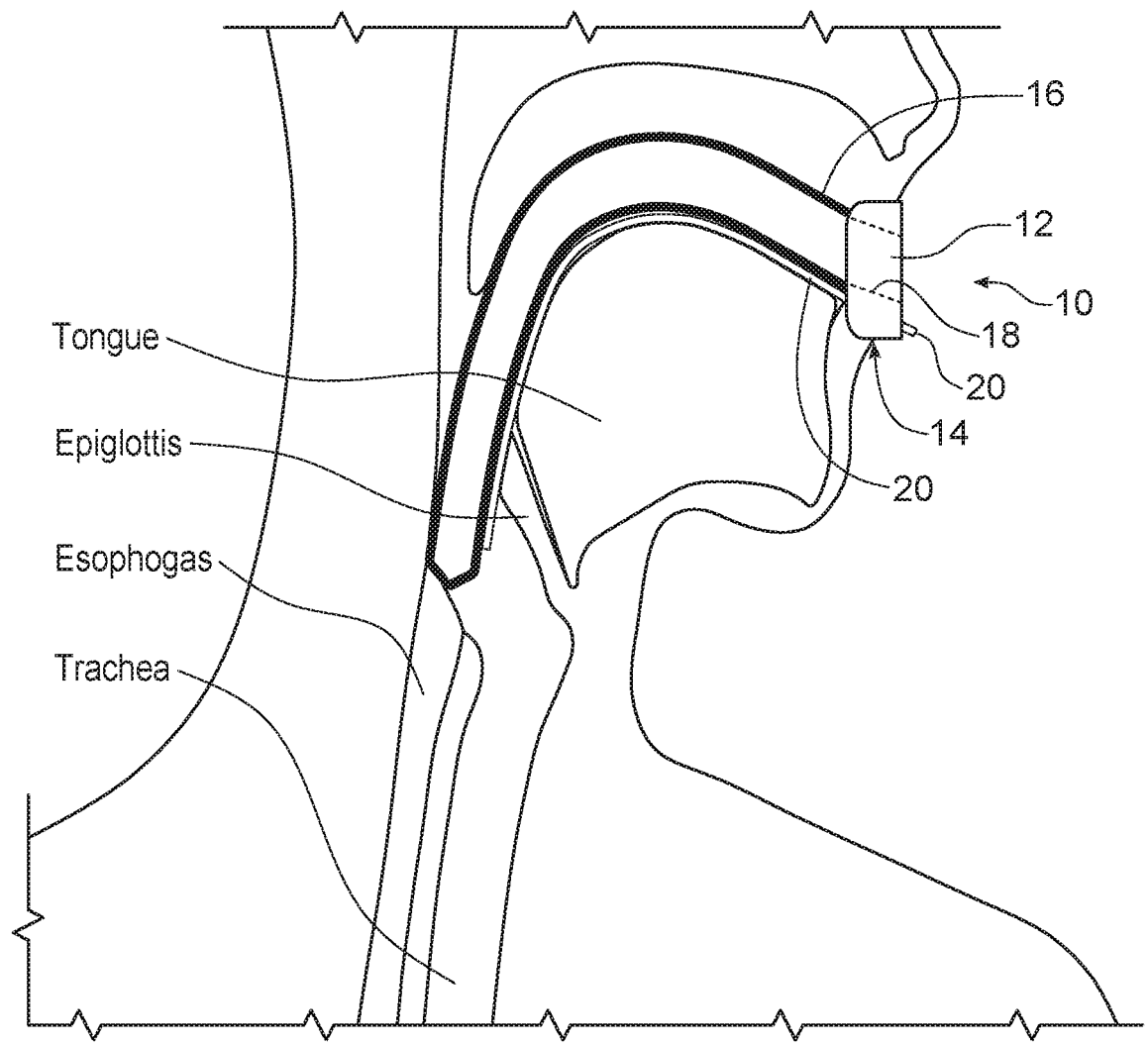

FIG. 1B shows the primary vine robot 16 in an actuated state. This phase commences as two sub-steps: first the primary vine robot 16 is inflated and grows toward the throat of the patient, away from the mouthpiece 12. FIG. 1C shows the primary vine robot 16 fully extended into the laryngopharynx. At this point, the intubation vine robot 20 is positioned to be inflated and grown. The intubation vine robot 20 can be pre-formed to approximate average anatomical structure.

Figure 1D:
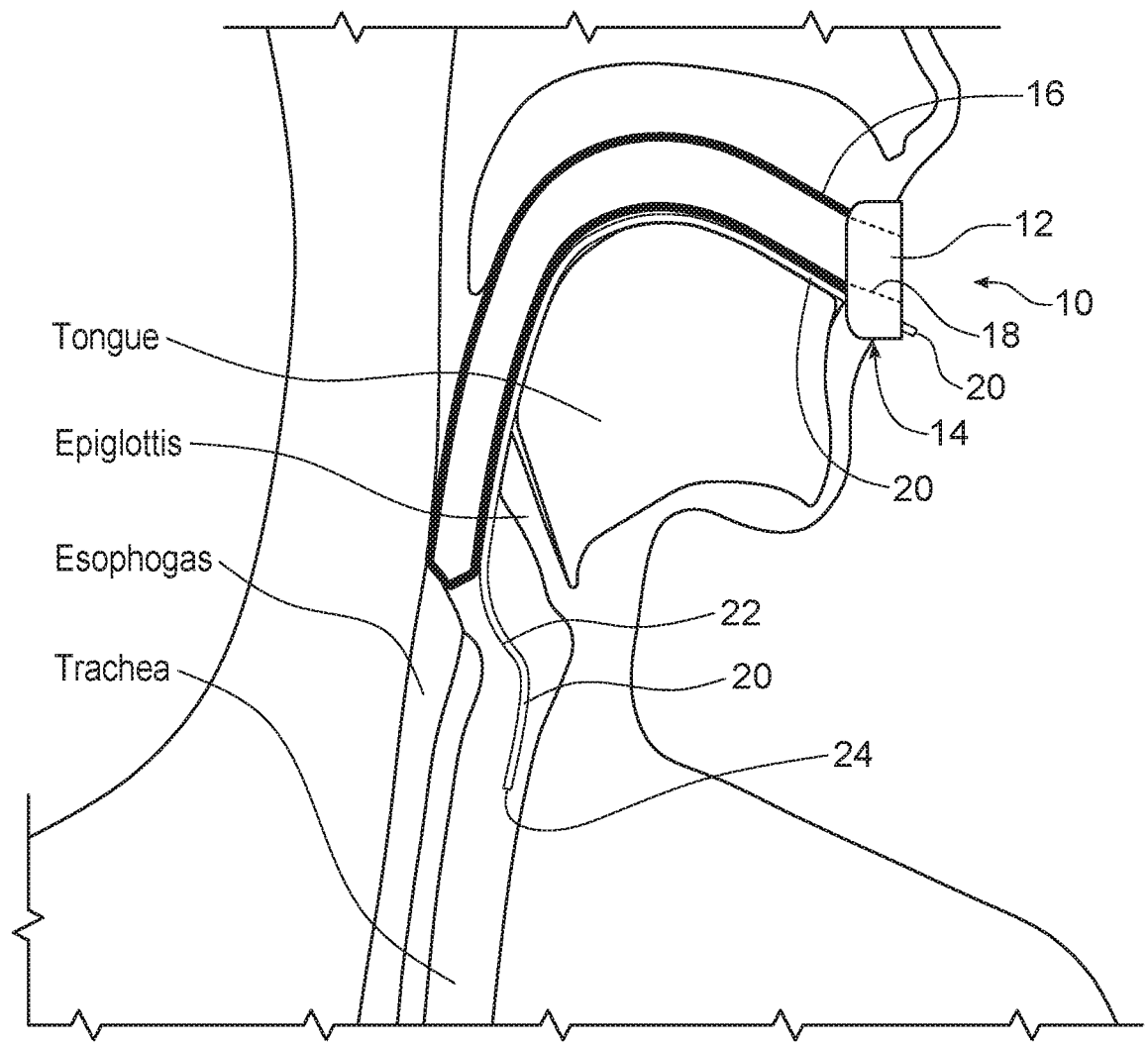
FIG. 1D illustrates the actuation of the intubation vine robot of FIG. 1A to provide a lumen through which a breathing tube is passed.
Figure 1E:
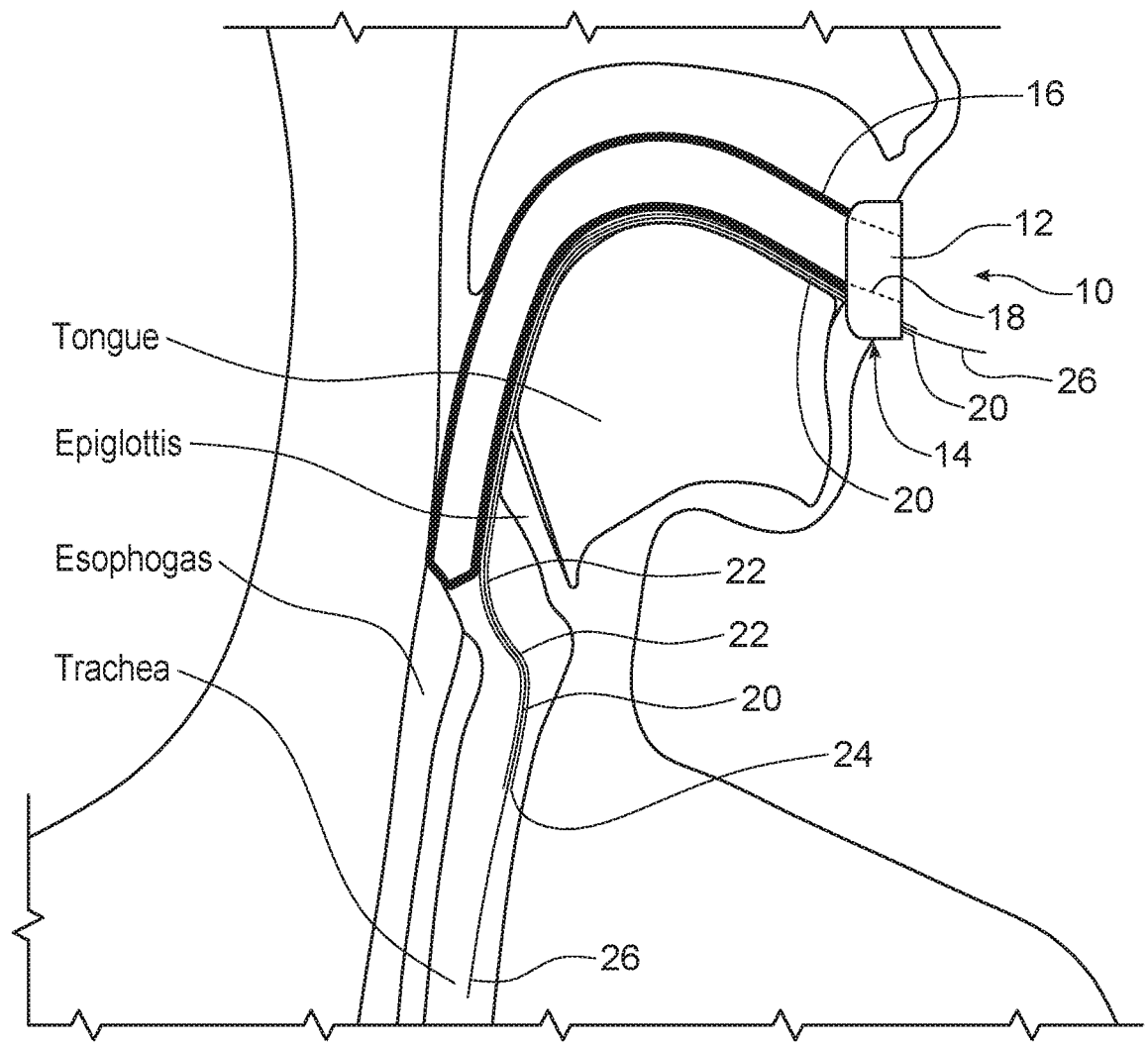
FIG. 1E illustrates the insertion of a breathing tube through the lumen generated by the extension of the intubation vine robot shown in FIG. 1D.

FIG. 1D shows the growth of intubation vine robot 20 into the trachea. As the intubation vine robot 20 grows, a predefined shape is preferably produced to orient the tip anteriorly towards the trachea. This intubation vine robot 20 can be pre-formed with one or two instances of curvature 22 (two are depicted in FIGS. 1D and 1E). The instances of curvature provide the predefined shape. As discussed in Hawkes et al. US Patent Publication US2019/0217908 and in the background of the application, curvatures can be provided in different ways, including controlling relative lengths of the wall material of the intubation vine robot 20 on different sides. An open distal end 24 of the intubation body allows for the production of a lumen through which a semi-rigid breathing tube can be passed.

FIG. 1E illustrates the passage of a breathing tube 26 through first through the mouthpiece 12 and second the lumen that was provided by extension of the intubation vine robot 20, allowing the breathing tube to easily pass through the lumen and into the patient's trachea. At this point, the device 10 can be removed from the patient and artificial breathing can commence. Another option instead of a tube is to include a valve to implement PEEP (positive-end expiatory pressure), which could be used instead of a breathing tube. If used, it is important to ensure that sufficient pressure is maintained so that the device will not collapse on itself during the exhalation. A breathing tube adds an additional component and step. However, it ensures a simple and reliable intubation, and can reduce the costs of the intubation vine robot device because the device need only be designed for delivery instead of supporting the breathing cycle.

Figure 2A:
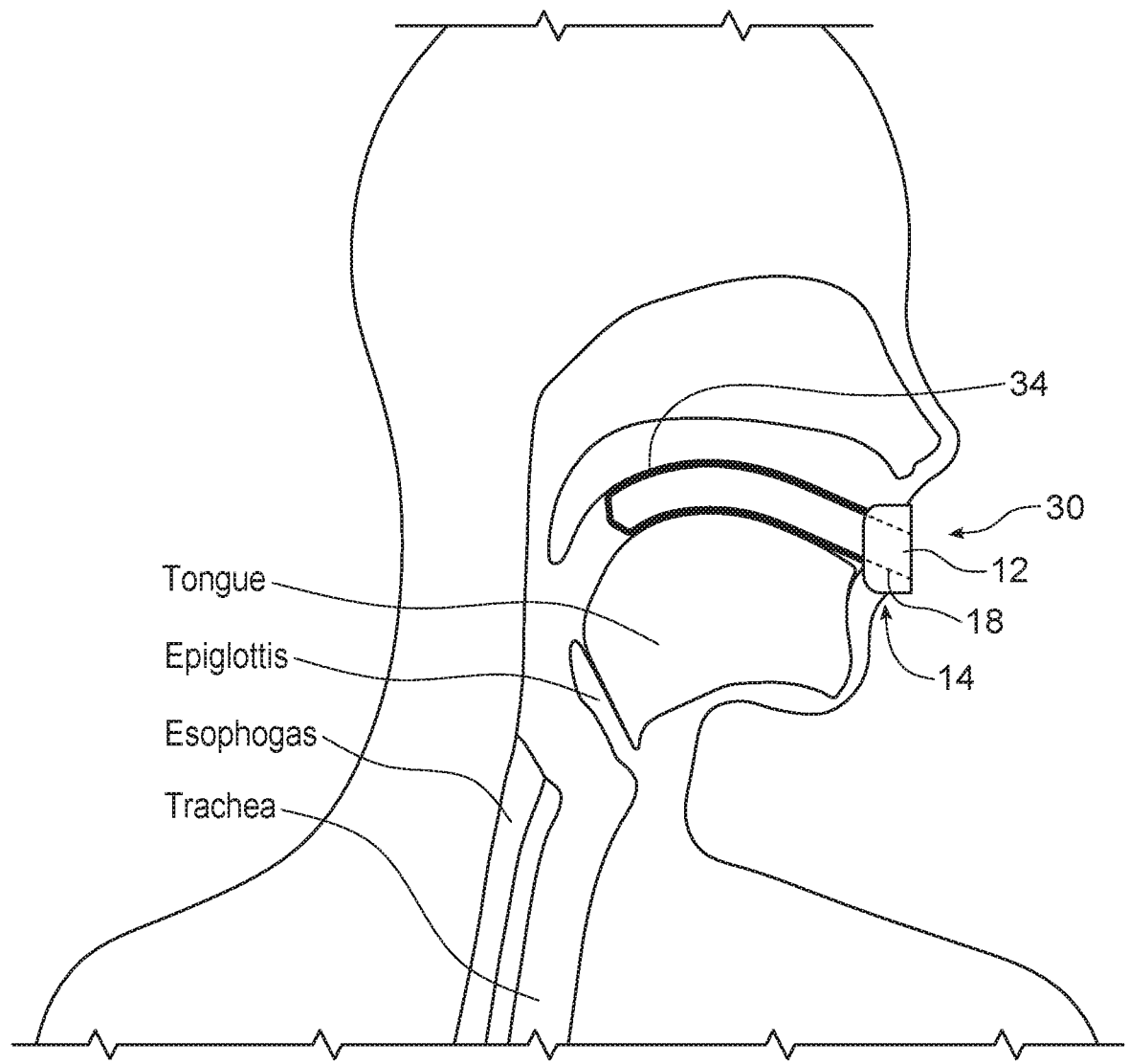
FIGS. 2A-2C are schematic diagrams of a preferred embodiment vine robot intubation device in partially and fully actuated states.
Figure 2B:
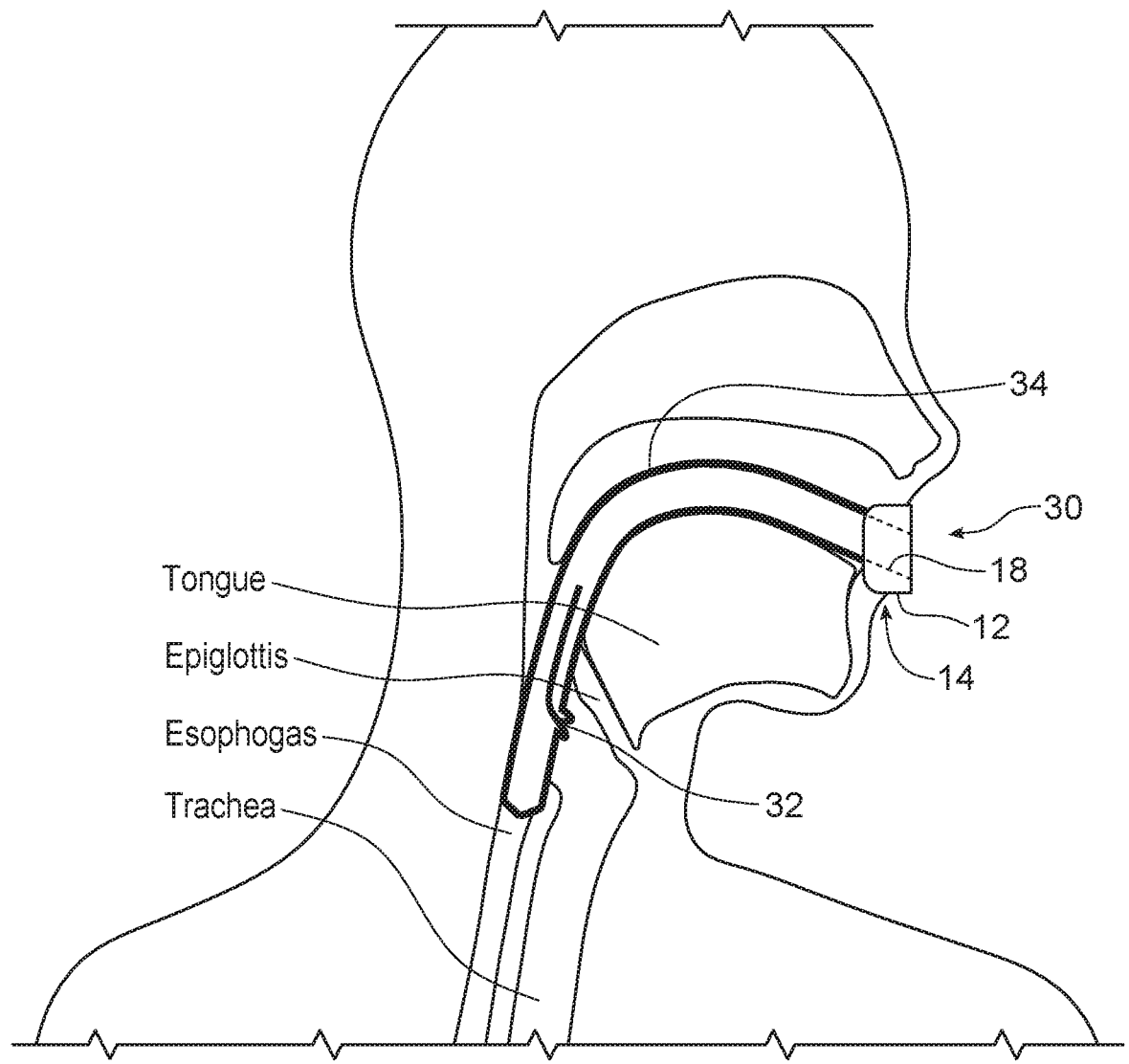
Figure 2C:
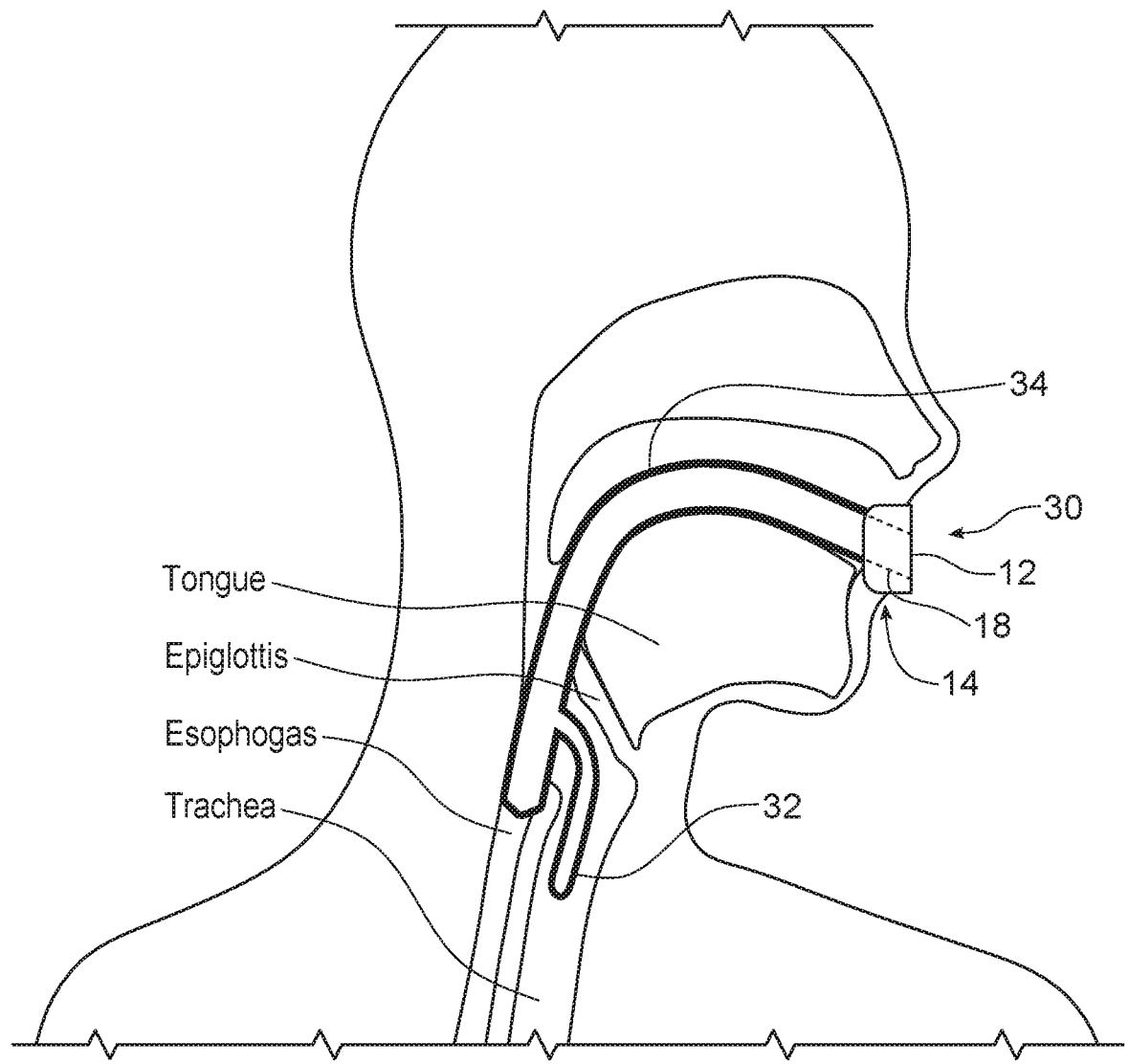

FIGS. 2A-2C illustration another preferred embodiment vine robot intubation device 30. Common reference numbers are used for common features shown in FIGS. 1A-1E. Operation is similar to the device 10 of FIGS. 1A-1E. In the device 30, an intubation vine robot 32 is formed unitarily with a primary vine robot 34, as branch that extends from a side wall of the primary vine robot 34. The intubation vine robot 32 includes a preformed curve section 36 to help align a lumen defined by it for passage of an air tube as in FIG. 1E. A breathing tube can be used. As another option, the intubation vine robot and primary vine robot 34 incorporate flexible material, self-expanding material, e.g. nitinol at the distal opening and a few locations to maintain a breathing lumen during the entire breathing cycle. Inflation overcomes the force of the self-expanding material during insertion, and then the self-expanding material maintains the opening. With the intubation robot 32 being a branch of the primary vine robot 34, it can be actuated via the same pressure source and lumen, such that a ventilator can simply pressurize the vine to deploy and continue ventilating thereafter with the fewest possible steps. Preferably, as shown in FIG. 2C, the primary vine robot 34 has a length that permits it to extend into the esophagus slightly. This helps to both secure the device 30 and to produce a seal to prevent aspiration, much like a laryngeal mask airway (LMA).

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A vine robot tracheal intubation device, comprising an everting primary vine robot attached to a mouthpiece and a smaller diameter everting intubation vine robot associated with the primary everting vine robot, wherein the primary vine robot is shaped and sized to extend to the back of a patient's laryngopharynx when fully actuated and the intubation everting vine robot is shaped and sized to extend from the primary vine robot into the patient's trachea when fully actuated, whereby a lumen is provided by the device from the mouthpiece into the patient's trachea, and
  wherein the intubation vine robot is formed unitarily with the primary vine robot and is configured to form a branch from the primary vine robot when extended;
  wherein the mouthpiece defines an access port to allow inflation of both of the primary soft robot and the intubation soft robot from a single pressure source.

2. The vine robot tracheal intubation device of claim 1, wherein a diameter of the primary vine robot is set such that while filling the oral cavity and oropharynx, it lifts a lower jaw of the patient and protrudes it forward and down.

3. The vine robot tracheal intubation device of claim 1, wherein the intubation vine robot comprises a pre-bent section configured to place and orient the lumen in the trachea.

4. The vine robot tracheal intubation device of claim 3, wherein the intubation vine robot is carried on an outer surface of the primary vine robot.

5. The vine robot tracheal intubation device of claim 4, wherein the intubation vine robot defines a lumen sized to pass a breathing tube therethrough.

6. The vine robot tracheal intubation device of claim 4, wherein the mouthpiece defines an access port to allow inflation of the primary vine robot.

7. The vine robot tracheal intubation device of claim 6, wherein the intubation vine robot extends through the mouthpiece.

8. The vine robot tracheal intubation device of claim 1, wherein the lumen is defined by both of the primary vine robot and intubation vine robot when extended.

9. The vine robot tracheal intubation device of claim 1, wherein the primary vine robot comprises a predetermined non-linear shape when extended.

10. The vine robot tracheal intubation device of claim 9, wherein the predetermined non-linear shape is configured to create pressure points to protrude the mandible, lift the epiglottis, and expose the trachea.

11. The vine robot tracheal intubation device of claim 1, wherein a distal tip of the intubation vine robot comprises a flexible, self-expanding material.

12. The vine robot tracheal intubation device of claim 11, wherein the flexible, self-expanding material is nitinol.

13. A method for intubation of a patient, the method comprising:
  inserting a mouthpiece attached to an everting primary vine robot and an intubation vine robot with both of the primary vine robot and an intubation vine robot in an unactuated position into the patient's mouth;
  applying fluid pressure into the primary vine robot to gradually evert and extend it into the back of the laryngopharynx of the patient;
  applying fluid pressure to extend the intubation vine robot into the trachea of the patient and provide a lumen from the mouthpiece to the trachea; and
  providing air or oxygen through the lumen into the trachea, wherein the providing comprises passing a breathing tube through the intubation vine robot and supplying the air or oxygen through the breathing tube.

14. The method of claim 13, comprising removing the mouthpiece, primary vine robot and the intubation vine robot while leaving the breathing tube in place prior to the providing.

15. The method of claim 13, wherein the providing comprises passing the air or oxygen through the lumen, which is defined by both of the primary vine robot and the intubation vine robot.

16. A vine robot tracheal intubation device, comprising an everting primary vine robot attached to a mouthpiece and a smaller diameter everting intubation vine robot associated with the primary everting vine robot, wherein the primary vine robot is shaped and sized to extend to the back of a patient's laryngopharynx when fully actuated and the intubation everting vine robot is shaped and sized to extend from the primary vine robot into the patient's trachea when fully actuated, whereby a lumen is provided by the device from the mouthpiece into the patient's trachea; and
  wherein the intubation vine robot is formed unitarily with the primary vine robot and is configured to form a branch from the primary vine robot when extended, and
  wherein the lumen is defined by both of the primary soft robot and the intubation soft robot when extended.

17. The vine robot tracheal intubation device of claim 16, wherein a diameter of the primary vine robot is set such that while filling the oral cavity and oropharynx, it lifts a lower jaw of the patient and protrudes it forward and down.

18. The vine robot tracheal intubation device of claim 16, wherein the intubation vine robot comprises a pre-bent section configured to place and orient the lumen in the trachea.

19. The vine robot tracheal intubation device of claim 16, wherein the lumen is defined by both of the primary vine robot and intubation vine robot when extended.

20. The vine robot tracheal intubation device of claim 16, wherein the primary vine robot comprises a predetermined non-linear shape when extended.

21. The vine robot tracheal intubation device of claim 16, wherein a distal tip of the intubation vine robot comprises a flexible, self-expanding material.

* * * * *